(12) United States Patent
Potter

(10) Patent No.: US 7,731,706 B2
(45) Date of Patent: Jun. 8, 2010

(54) TRUE ANGULAR CATHETER SHAFT DEFLECTION APPARATUS

(75) Inventor: Daniel J. Potter, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 11/647,489

(22) Filed: Dec. 29, 2006

(65) Prior Publication Data

US 2008/0161775 A1    Jul. 3, 2008

(51) Int. Cl.
*A61M 25/00* (2006.01)

(52) U.S. Cl. ....................................................... 604/523

(58) Field of Classification Search .......... 604/523–528
See application file for complete search history.

(56) References Cited

U.S. PATENT DOCUMENTS 5,507,725 A * 4/1996 Savage et al. ............. 604/95.04
6,500,167 B1 * 12/2002 Webster, Jr. .................. 604/528
6,837,867 B2 * 1/2005 Kortelling ................. 604/95.04
2005/0283135 A1 * 12/2005 Pepin ........................... 604/525

OTHER PUBLICATIONS

Pepin, Henry J., "Catheter incorporating a curable polymer layer to control flexiblity and method of manufacture", 2005-0283135.

* cited by examiner

*Primary Examiner*—Kevin C Sirmons
*Assistant Examiner*—Deanna K Hall
(74) *Attorney, Agent, or Firm*—Dykema Gossett PLLC

(57) ABSTRACT

The invention relates to a steerable catheter having a distal section with reduced variation in deflection path during deflection. The distal section of the catheter includes stripes of different material hardness along the length of the distal section affecting the directionality of catheter deflection upon the application of a deflection force like that applied by pull wires. The stripes result in preferential bending in a desired path with greater reproducibility.

26 Claims, 4 Drawing Sheets

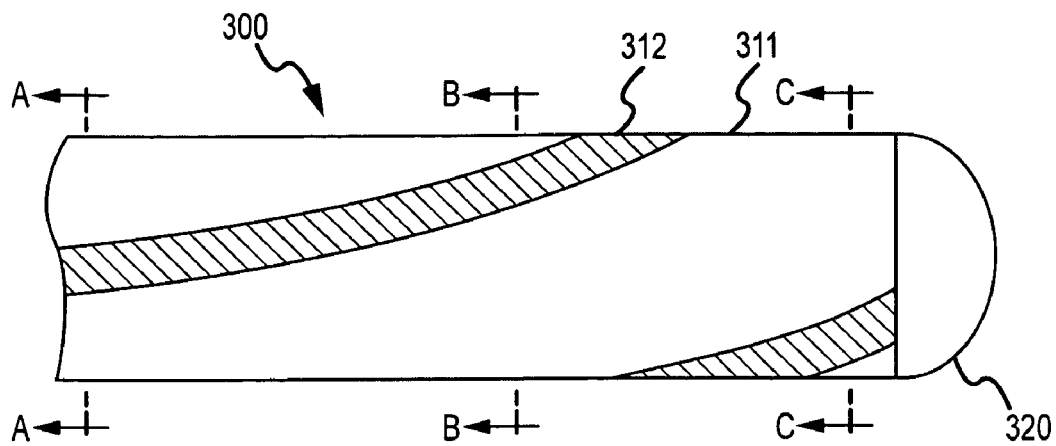
FIG.3
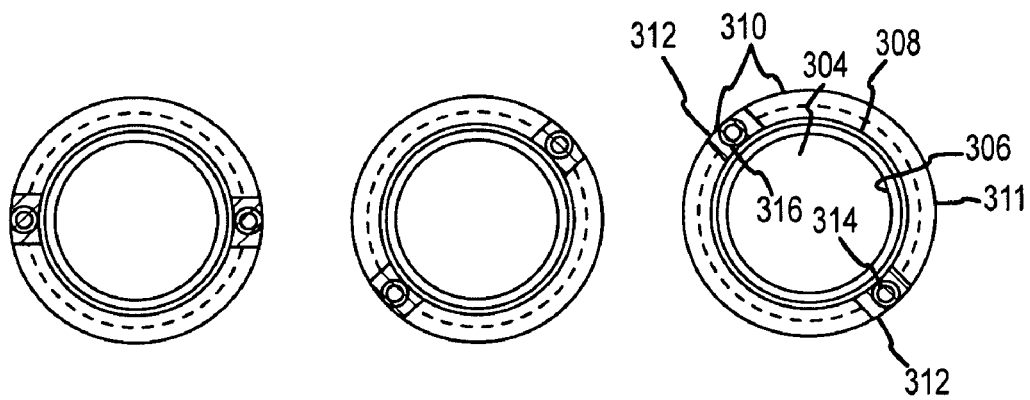
FIG.4a
A-A
FIG.4b
B-B
FIG.4c
C-C
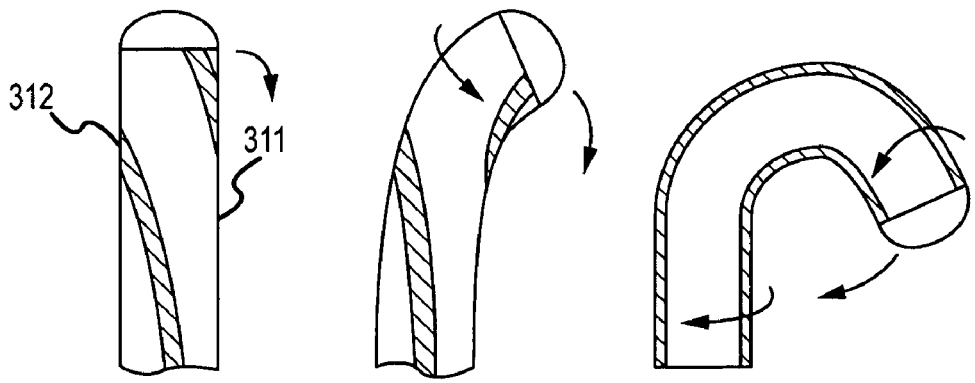
FIG.5a    FIG.5b    FIG.5c

A-A

B-B

C-C

A-A

B-B

C-C

TRUE ANGULAR CATHETER SHAFT DEFLECTION APPARATUS

BACKGROUND OF THE INVENTION a. Field of the Invention

The instant invention relates to catheters. In particular, the instant invention relates to a catheter with a steerable distal section having reduced variation in planarity during deflection.

b. Background Art

It is well-known that the pumping action of the heart is controlled by electrical stimulation of myocardial tissue. Stimulation of this tissue in various regions of the heart is controlled by a series of conduction pathways contained within the myocardial tissue.

Cardiac arrhythmias arise when the pattern of the heartbeat is changed by abnormal impulse initiation or conduction in the myocardial tissue. Such disturbances often arise from additional conduction pathways which are present within the heart either from a congenital developmental abnormality or an acquired abnormality which changes the structure of the cardiac tissue, such as a myocardial infarction.

One of the ways to treat such disturbances is to identify the conductive pathways and to sever part of this pathway by destroying these cells which make up a portion of the pathway. Traditionally, this has been done by either cutting the pathway surgically; freezing the tissue, thus destroying the cellular membranes; or by heating the cells, thus denaturing the cellular proteins. The resulting destruction of the cells eliminates their electrical conductivity, thus destroying, or ablating, a certain portion of the pathway. By eliminating a portion of the pathway, the pathway may no longer maintain the ability to conduct, and the arrhythmia ceases.

The success and advancement of current therapies is dependent upon the development and use of more precise localization techniques which allow accurate anatomical determination of abnormal conductive pathways and other arrythmogenic sites. Historically, the electrophysiologist has had to compromise between placing the catheter in the place of greatest clinical interest and areas that are anatomically accessible.

One area of advancement in improving localization techniques and accessing additional sites includes the use of curved and steerable catheters. Curved catheters offer improved maneuverability to specific, otherwise inaccessible sites by being shaped specifically to access a particular site. Although perhaps useful for some more accessible sites, the use of this type of catheter has limitations in reaching sites requiring active articulation during placement. Steerable catheters, which may also be pre-curved, proved additional advantages.

While steerability of catheters has improved, there is a need to eliminate significant variations in planarity during deflection of the distal tips of catheters. In accordance with this invention, a catheter is provided that addresses and potentially eliminates significant variation in planarity during catheter tip deflection. The invention also offers a catheter capable of a multitude of angular shaft deflection trajectories through a two or three dimensional range including a catheter that could initially be straight and, upon complete deflection, turn into a loop-shaped catheter. This invention would improve product reliability, consistency, and performance, as well as improve safety of electrophysiology ablation or diagnostic procedures.

BRIEF SUMMARY OF THE INVENTION

It is desirable to eliminate significant variations in planarity during deflection of the distal sections of catheters. In particular, it is desirable to have a catheter capable of a multitude of angular shaft deflection trajectories or paths through a two or three dimensional range.

An embodiment of the invention is a catheter comprising a distal section constructed of materials of different material hardness longitudinally placed along the distal section to aid bending deflection of the distal section along a desired path, wherein the materials of different material hardness form a wall creating a lumen, and the distal section has a distal end and a proximal end.

The distal section of the catheter may include a softer material placed adjoining a harder material in a lengthwise direction. The width of the softer material may vary in steps or graduations in the lengthwise direction. Alternatively, the hardness of the softer material may vary in a lengthwise direction. The location of the softer material may also vary in a lengthwise direction. Further, multiple pairs or layers of sections, of softer material may provide multiple planes of deflection and asymmetrical shaft deflection.

The catheter may further include pullwires fixed in the distal section at the distal end. The pullwires may be further accompanied by a system to provide actuation forces to deflect the distal section of the catheter via a handle actuator. The pullwires may also be aligned with the softer material and the pullwires may be housed within the softer material or within the wall of harder material, proximate to the softer material. The pullwires may also be housed within the lumen.

The catheter may further include a component in the distal section to prevent collapse of the wall of the distal section.

The catheter may further comprise a braiding material incorporated into the materials of different hardness to provide radial stability in the distal section.

The materials of different hardness may be co-extruded, reflowed, thermally bonded, etc.

BRIEF DESCRIPTION OF THE DRAWINGS

FIG. 3 is a side view of an embodiment of a catheter distal section according to the present invention having spiral stripes of material having hardness that is different from the remainder of the catheter shaft.

FIG. 4(a) is a transverse cross-sectional view of the catheter distal section of FIG. 3 taken along line A-A of FIG. 3.

FIG. 4(b) is a transverse cross-sectional view of the catheter distal section of FIG. 3 taken along line B-B of FIG. 3.

FIG. 4(c) is a transverse cross-sectional view of the catheter distal section of FIG. 3 taken along line C-C of FIG. 3.

FIG. 5(a) is a side view of the catheter distal section of FIG. 3 in an undeflected configuration.

FIG. 5(b) is a side view of the catheter distal section of FIG. 3 in an partially deflected configuration.

FIG. 5(c) is a side view of the catheter distal section of FIG. 3 in an deflected configuration.

FIG. 7(*b*) is a transverse cross-sectional view of the catheter distal section of FIG. 5 taken along line B-B of FIG. 6.

FIG. 7(*c*) is a transverse cross-sectional view of the catheter distal section of FIG. 5 taken along line C-C of FIG. 6.

FIG. 8(*b*) is a side view of the catheter distal section of FIG. 6 in an partially deflected configuration.

FIG. 8(*c*) is a side view of the catheter distal section of FIG. 6 in an deflected configuration.

FIG. 10(*b*) is a transverse cross-sectional view of the catheter distal section of FIG. 9 taken along line B-B of FIG. 9.

FIG. 10(*c*) is a transverse cross-sectional view of the catheter distal section of FIG. 9 taken along line B-B of FIG. 9.

FIG. 11(*b*) is a side view of the catheter distal tip of FIG. 9 in an partially deflected configuration.

FIG. 11(*c*) is a side view of the catheter distal tip of FIG. 9 in a further deflected configuration.

DETAILED DESCRIPTION OF THE INVENTION

Several embodiments of a catheter distal tip deflection apparatus are depicted in the figures. As described further below, the catheter distal tip deflection apparatus according to the present invention provides a number of advantages, including, for example, reducing or eliminating significant variation in deflection path during shaft deflection, the ability to construct a catheter capable of a multitude of angular shaft deflection trajectories through a two or three dimensional range, improved product reliability, improved consistency and performance, and improved safety of electrophysiology ablation and diagnostic procedures.

Figure 1:
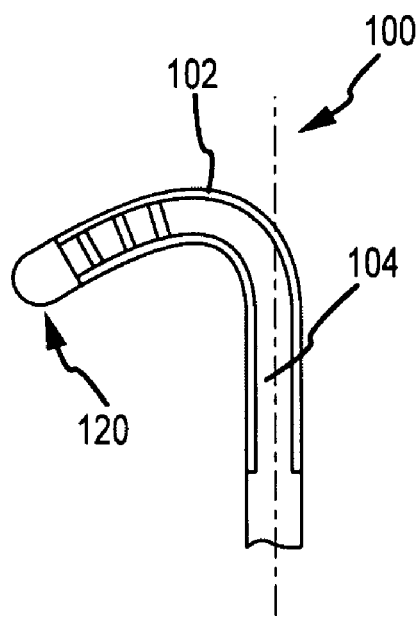
FIG. 1 is a side view of a distal section of the catheter according to the present invention.
Figure 2:
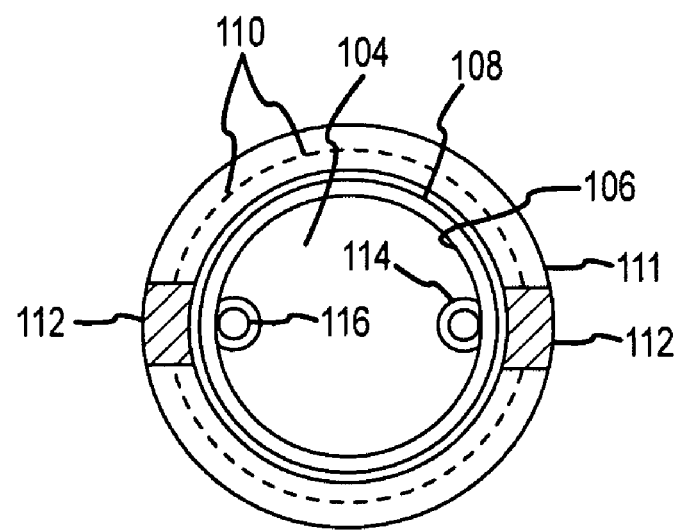
FIG. 2 is an end cross-sectional view of the catheter distal section of FIG. 1.
Figure 6:
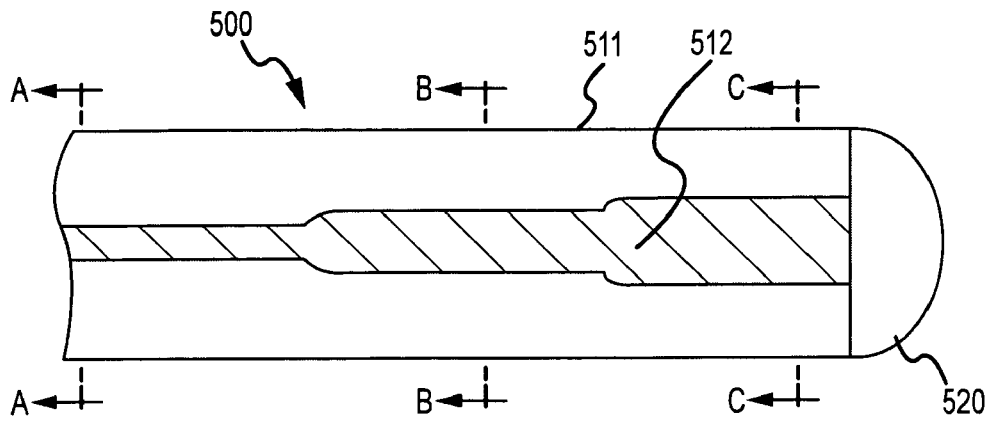
FIG. 6 is a side view of an embodiment of a catheter distal section having stepped-width stripes of different material hardness according to the present invention.

Referring to FIGS. 1 and 2, a single axis steerable catheter distal section 100 is disclosed in accordance with this invention. The catheter distal section 100 comprises a tubular body 102 defining a lumen or bore 104, and a tip electrode 120. As shown in FIG. 2, which is a transverse cross-sectional view of the tubular body 102, the tubular body 102 may comprise an inner coil 106, a PTFE sleeve 108 outside the inner coil 106, and a braiding material 110 within a polymer sleeve 111 and two longitudinally-extending stripes 112 of material that is different from the remainder of the material of polymer sleeve 111 outside the PTFE sleeve 108. The stripes 112 are offset 180° from each other and are made of material having a lower durometer than that of the polymer sleeve 111. The stripes 112 may be located along the polymer sleeve 111 by co-extrusion, although those skilled in the art will understand that other means of fabrication are possible. The polymer sleeve 111 may be constructed from 50-55D Pebax®, while the stripes 112 may be constructed from 35-40D Pebax®. The braiding may be stainless steel or Kevlar®, for example. Although referred to as the "PTFE sleeve 108," the sleeve 108 may be made of any material with similar qualities. The inner coil 106 helps to prevent collapse of catheter distal tip 100 when it is deflected.

Inside the tubular body 102, in the plane formed by stripes 112, are two or more pullwire sleeves 114 to house multiple pullwires 116. Alternatively, the pullwire sleeves may instead be imbedded in the stripes 112, the stripes 112 constructed in such a manner to house the pullwires 116. The pullwire sleeves 114 may be made of a number of polymers or rubbers. The pullwire sleeves 114 house the pullwires 116, which run the length of the catheter body to a control means at the proximal end of the catheter body and may be anchored at or near the tip electrode 120. The distal section may further comprise a compression coil to maintain circumferential integrity and facilitate deflection. Exemplary control means are shown in U.S. Pat. Nos. 5,395,329; 5,861,024; and 6,308,090; the disclosures of which are incorporated herein by reference.

The difference in durometer between the polymer sleeve 111 and the stripes 112, combined with the location of the pullwires 116 in the same plane as the stripes 112 180° apart ensures angular deflection of catheter distal section 100 because the lower durometer stripes 112 stretch and compress more readily than the higher durometer polymer sleeve 111. Thus, tension on one of the pullwires 116 causes the catheter tip 100 to bend in the plane defined by stripes 112.

Although not shown, the catheter distal section 100 could have two pairs each of stripes and pullwires, allowing a user to deflect the catheter distal section in two separate planes. In this embodiment, the stripes and pullwires would be spaced equidistant across the circumference of the catheter distal section. Manipulation of the first pair of pullwires would deflect the catheter distal section along a first plane, while manipulation of the second pair of pullwires would deflect the catheter distal section along a second plane.

Signal wires for supplying energy to the tip electrode 120 are not shown, but can be located in the lumen 104. The distal section may comprise multiple lumen 104.

While the embodiment of FIGS. 1 and 2 has straight stripes 112, FIGS. 3 and 4(*a*)-(*c*) show a catheter distal section 300, with spiral or helical stripes 312 of lower durometer than the durometer of the polymer sleeve 311.

FIG. 3 shows the outside of the tubular body 302 of the catheter distal section 300, showing the stripes 312 spiraling around the polymer sleeve 311. Three transverse cross-sections, A-A, B-B, and C-C are cut at various points along the length of the catheter distal section 300. The corresponding transverse cross-sectional views are shown at FIGS. 4(*a*)-(*c*), respectively.

As shown in FIGS. 4(*a*)-(*c*), the tubular body 302 may comprise an inner coil 306, a PTFE sleeve 308 around the outside of inner coil 306, and a braiding material 310 within the polymer sleeve 311 or alternatively, at the inside diameter of the polymer sleeve 311, and the two stripes 312 around the outside of the PTFE sleeve 308. The stripes 312 are located 180° from each other along the circumference of the distal section 300 and are made of lower durometer material than the material from which the polymer sleeve 311 is constructed. For example, the polymer sleeve 311 may be 50-55D Pebax®, while the stripes 312 may be 35-40D Pebax®. The braiding may be stainless steel or Kevlar®, for example. Although referred to as the "PTFE sleeve 308," the sleeve 308 may be made of any material with qualities similar to those described herein. The inner coil 306 helps to prevent collapse of the catheter distal tip 300 when it is deflected.

Rather than having separate pullwire sleeves inside the tubular body 302, the pullwire sleeves 314 are integral with the stripes 312 in the embodiment depicted in FIGS. 3 and 4(*a*). The pullwire sleeves 314 house the pullwires 316, which run the length of the catheter body to a control means at the proximal end of the catheter body and may be anchored at or near the electrode 320.

The construction of the stripes 312 with a material of lower durometer than the material of the polymer sleeve 311, in combination with the spiral arrangement of co-extruded stripes 312 around the polymer sleeve 311, allow a user to form complex curves along multiple planes with the catheter distal section by pulling the pullwires 316 as shown in FIGS. 5(a)-(c).

Figure 7A:
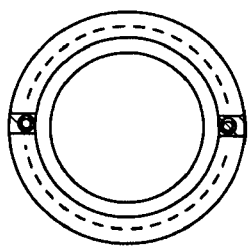
FIG. 7(*a*) is a transverse cross-sectional view of the catheter distal section of FIG. 5 taken along line A-A of FIG. 6.
Figure 7B:
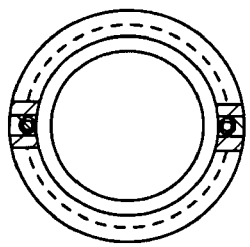
Figure 7C:
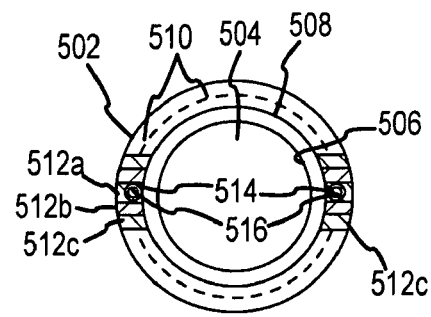

FIGS. 6, 7(a)-(c), and 8(a)-(c) show another embodiment of a catheter according to the present invention. Referring to FIGS. 6, 7(a)-(c), and 8(a)-(c), a single-axis steerable catheter distal section 500 is disclosed. The catheter distal tip 500 comprises a tubular body 502 defining a lumen or bore 504, and a tip electrode 520. Transverse cross-sections A-A, B-B, and C-C are cut at various points along the length of catheter distal tip 500. The corresponding cross-sectional views are shown at FIGS. 7(a)-(c), respectively.

FIGS. 7(a)-(c) are transverse cross-sectional views of tubular body 502. Tubular body 502 may comprise an inner coil 506, a PTFE sleeve 508 around the outside of inner coil 506, and a braiding material 510 within a polymer sleeve 511 or alternatively, at the inside diameter of the polymer sleeve 511, and the two stripes 512 along the outside of the PTFE sleeve 508. The stripes 512 are located 180° from each other along the circumference of the distal section 500 and are made of a matrix having lower durometer than the durometer of the material from which the polymer sleeve 511 is constructed. For example, the polymer sleeve 511 may be 50-55D Pebax®, while the stripes 512 may be 35-40D Pebax®. The braiding may be stainless steel or Kevlar®, for example. Although referred to as the "PTFE sleeve 508," the sleeve 508 may be made of any material with similar qualities to those described herein. Inner coil 506 helps to prevents collapse of catheter distal section 500 when it is deflected.

As shown in FIGS. 6 and 7(a)-(c), the width of the stripes 512 is greater closer to the tip electrode 520 at the distal end of catheter distal section 500 when compared to the width of the stripes 512 at the proximal end of the distal section 500. A greater width of stripes 512 provides for greater deflection of the catheter distal section 500 near the distal end for a given tension on a pullwire 516 when compared to the same section of the catheter distal section 500 with stripes 512 of narrower width.

The pullwire sleeves 514 are shown embedded in stripes 512, although they also could be located inside the tubular body 502 as in the embodiment shown in FIGS. 1 and 2. The pullwire sleeves 514 house the pullwires 516, which run the length of the catheter body to a control means at the proximal end of the catheter body and may be anchored at or near the electrode 520. The stripes 512 may also be constructed of materials varying in durometer to produce the same effect.

Figure 8A:
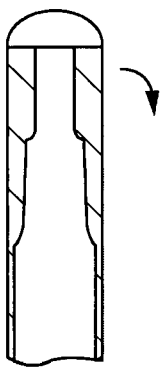
FIG. 8(*a*) is a side view of the catheter distal section of FIG. 6 in an undeflected configuration.
Figure 8B:
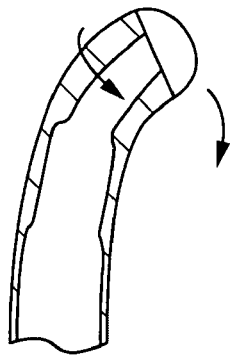
Figure 8C:
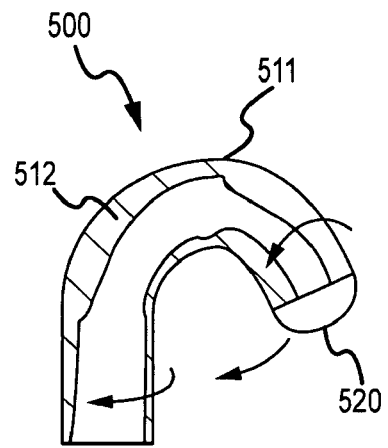
Figure 9:
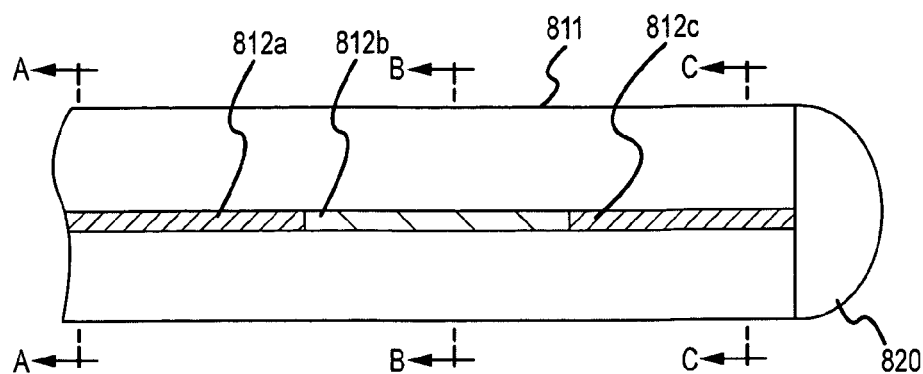
FIG. 9 is a side view of an embodiment of a catheter distal section having stripes of different material hardness according to the present invention.

FIGS. 8(a)-(c) show the distal end of the catheter distal section 500 deflected as a result of pulling a pullwire 516. The angular deflection of distal end of the distal section 500 increases with increased width of stripes 512—in this case moving toward the distal end of the catheter distal section 500, approaching the tip electrode 520.

Although not shown, the catheter distal section 500 could have two pairs each of stripes (four total) and pullwires, allowing a user to deflect the catheter distal section in two separate planes. In this embodiment, the stripes and pullwires would be spaced equidistant across the circumference of the catheter distal section. Manipulation of the first pair of pullwires would deflect the catheter distal section along a first plane, while manipulation of the second pair of pullwires would deflect the catheter distal section along a second plane.

Figure 10A:
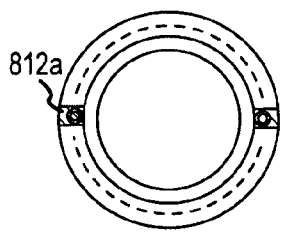
FIG. 10(*a*) is a transverse cross-sectional view of the catheter distal section of FIG. 9 taken along line A-A of FIG. 9.
Figure 10B:
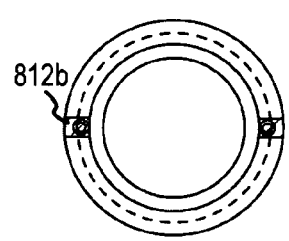
Figure 10C:
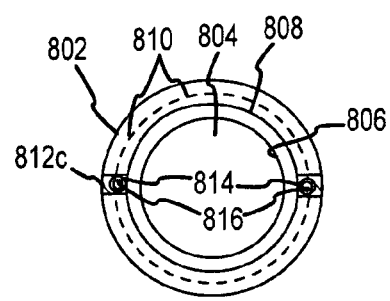
Figure 11A:
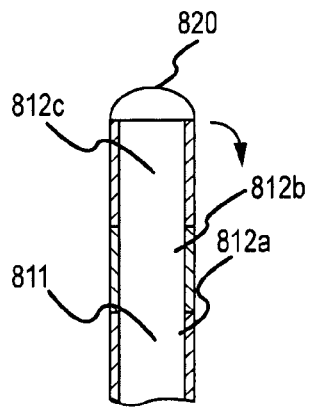
FIG. 11(*a*) is a side view of the catheter distal tip of FIG. 9 in an undeflected configuration.
Figure 11B:
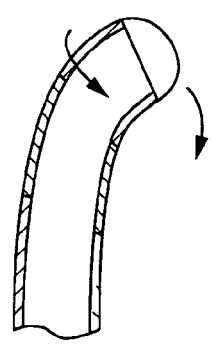
Figure 11C:
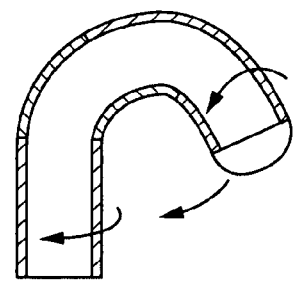

FIGS. 9, 10(a)-(c), and 11(a)-(c) show another embodiment of the catheter construction according to the present invention. Referring to FIGS. 9, 10(a)-(c), and 11(a)-(c), a single-axis steerable catheter distal section 800 is shown. The catheter distal section 800 may comprise a tubular body 802 defining a lumen or bore 804, and a tip electrode 820. Transverse cross-sections A-A, B-B, and C-C are cut at various points along the length of catheter distal section 800. The corresponding cross-sectional views are shown at FIGS. 10(a)-(c), respectively.

FIGS. 10(a)-(c) are transverse cross-sectional views of tubular body 802. The tubular body 802 comprises an inner coil 806, a PTFE sleeve 808 around the outside of the inner coil 806, and a braiding material 810 within a polymer sleeve 811, or alternatively, at the inside diameter of the polymer sleeve 811, and the two stripes 812 (including stripe sections 812a, 812b, and 812c) on the outside of the PTFE sleeve 808. The stripes 812a, 812b, and 812c are located equidistant from each other across the circumference of the tubular body 802 and are made of lower durometer material than the material from which the polymer sleeve 811 is constructed. For example, the polymer sleeve 811 may be made of 50-55D material, while the stripes 812a, 812b, and 812c may be made of material of 50D, 40D, and 35D, respectively. The braiding may be stainless steel or Kevlar®, for example. Although referred to as the "PTFE sleeve 808," the sleeve 808 may be made of any material with similar qualities to those described herein. The inner coil 806 helps to prevent collapse of catheter distal tip 100 when it is deflected.

As stated above, the Durometer of the stripes 812a, 812b, and 812c may decrease in steps as they are located closer to the tip electrode 820 at the distal end of catheter distal section 800. The angular deflection of distal end of the distal section 800 increases with decreased durometer of the stripes 812a, 812b, and 812c—in this case moving toward the distal end of the catheter distal section 800, approaching the tip electrode 820.

The pullwire sleeves 814 are shown embedded in the stripes 812, although they also could be located inside the tubular body 802 as in the embodiment shown in FIGS. 1 and 2. The pullwire sleeves 814 house the pullwires 816, which run the length of the catheter body to a control means at the proximal end of the catheter body and may anchored at or near electrode 820.

Although not shown, the catheter distal section 800 could have two pairs each of stripes and pullwires, allowing a user to deflect the catheter distal section in two separate planes. In this embodiment, the stripes and pullwires would be spaced equidistant across the circumference of the catheter distal section. Manipulation of the first pair of pullwires would deflect the catheter distal section along a first plane, while manipulation of the second pair of pullwires would deflect the catheter distal section along a second plane.

Although the embodiments described above specifically describe the tip of the catheter, it will be understood by those skilled in the art that the catheter tip is only a portion of a complete system that may also include, e.g., control means or an irrigation system. In addition, rather than using an electrode for ablation, the catheter may use ultrasonic methods of ablation. The catheter tip disclosed may be used for any purpose for which a medical catheter is used including, but not limited to, diagnostics. It will further be understood by those skilled in the art that the present invention may be sold as a kit including other elements used with the catheter such as electronic components used in imaging.

Although several embodiments of this invention have been described above with a certain degree of particularity, those skilled in the art could make numerous alterations to the disclosed embodiments without departing from the spirit or scope of this invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising:
an elongated catheter body having a proximal end and a distal end, and at least one lumen in a longitudinal direction of the elongated catheter body, the elongated catheter body including a distal section near the distal end;
wherein the distal section includes a plurality of circumferential segments disposed adjacent to each other in a circumferential direction, the circumferential segments each having a circumferential span less than 360 degrees and extending in the longitudinal direction to form an outer wall of the distal section, a first one of the circumferential segments containing a material having a material hardness different from a material hardness of a material in a second one of the circumferential segments, the outer wall formed by the circumferential segments providing a change in material hardness in the circumferential direction between the first circumferential segment and the second circumferential segment.

2. The catheter of claim 1, wherein the plurality of circumferential segments include a soft circumferential segment that includes a material of lower material hardness than a material of one or more circumferential segments adjacent to the soft circumferential segment.

3. The catheter of claim 2, wherein the soft circumferential segment has a circumferential span that is significantly smaller than a total circumferential span of 360° of the distal segment.

4. The catheter of claim 2, wherein the soft circumferential segment has a circumferential span, and wherein the distal segment further includes a pullwire connection disposed in the circumferential span of the soft circumferential segment.

5. The catheter of claim 4, wherein the pullwire connection is a pullwire sleeve formed within the soft circumferential segment.

6. The catheter of claim 2, wherein the soft circumferential segment is a straight segment oriented along the longitudinal direction.

7. The catheter of claim 2, wherein the soft circumferential segment is a helical segment oriented in a helical direction around a longitudinal axis of the distal segment.

8. The catheter of claim 2, wherein the soft circumferential segment has a circumferential span that increases in size in the longitudinal direction from a proximal end toward a distal end of the soft circumferential segment.

9. The catheter of claim 2, wherein the soft circumferential segment decreases in material hardness in the longitudinal direction from a proximal end to a distal end of the soft circumferential segment.

10. The catheter of claim 9, wherein the soft circumferential segment has a plurality of longitudinal portions along the longitudinal direction of the soft circumferential segment, the longitudinal portions including different materials of different material hardness.

11. The catheter of claim 1, wherein the distal section includes a first pair of soft circumferential segments that are disposed about 180° from one another and are spaced from one another by circumferential segments that are higher in material hardness than the first pair of soft circumferential segments.

12. The catheter of claim 1, further comprising a distal electrode disposed at the distal end of the elongated catheter body.

13. A catheter comprising:
an elongated catheter body having a proximal end and a distal end, and at least one lumen in a longitudinal direction of the elongated catheter body, the elongated catheter body including a distal section near the distal end;
wherein the distal section includes a plurality of circumferential segments, the circumferential segments each having a circumferential span less than 360 degrees and extending in the longitudinal direction to form an outer wall of the distal section,
wherein the distal section includes a first pair of soft circumferential segments that are disposed about 180° from one another and are circumferentially spaced from one another by circumferential segments that are higher in material hardness than the first pair of soft circumferential segments.

14. The catheter of claim 13, wherein the first pair of soft circumferential segments are generally identical in size and material.

15. The catheter of claim 13, wherein the first pair of soft circumferential segments each have a circumferential span, and wherein the distal segment further includes a first pair of pullwire connections disposed in the circumferential spans of the first pair of soft circumferential segments.

16. The catheter of claim 13, wherein the distal section includes a second pair of soft circumferential segments that are disposed about 180° from one another and are spaced from one another by circumferential segments that are higher in material hardness than the second pair of soft circumferential segments, the second pair of soft circumferential segments being spaced by about 90° from the first pair of soft circumferential segments.

17. The catheter of claim 16, wherein the second pair of soft circumferential segments each have a circumferential span, and wherein the distal segment further includes a second pair of pullwire connections disposed in the circumferential spans of the second pair of soft circumferential segments.

18. The catheter of claim 13, wherein the first pair of soft circumferential segments each have a circumferential span that increases in size in the longitudinal direction from a proximal end toward a distal end of each of the soft circumferential segments.

19. The catheter of claim 13, wherein the first pair of soft circumferential segments each decrease in material hardness in the longitudinal direction from a proximal end toward a distal end of each of the soft circumferential segments.

20. A catheter comprising:
an elongated catheter body having a proximal end and a distal end, and at least one lumen in a longitudinal direction of the elongated catheter body, the elongated catheter body including a distal section near the distal end;
wherein the distal section includes a plurality of circumferential segments disposed adjacent to each other in a circumferential direction, the circumferential segments each having a circumferential span less than 360 degrees and extending in the longitudinal direction to form an outer wall of the distal section, wherein the distal section includes a soft circumferential segment that is adjacent one or more circumferential segments that are higher in material hardness than the soft circumferential segment.

21. The catheter of claim 20, wherein the soft circumferential segment has a circumferential span that is significantly smaller than a total circumferential span of 360° of the distal segment.

22. The catheter of claim 20, wherein the soft circumferential segment has a circumferential span, and wherein the distal segment further includes a pullwire connection disposed in the circumferential span of the soft circumferential segment.

23. The catheter of claim 20, wherein the soft circumferential segment is a helical segment oriented in a helical direction around a longitudinal axis of the distal segment.

24. The catheter of claim 20, wherein the soft circumferential segment has a circumferential span that increases in size in the longitudinal direction from a proximal end toward a distal end of the soft circumferential segment.

25. The catheter of claim 20, wherein the soft circumferential segment decreases in material hardness in the longitudinal direction from a proximal end to a distal end of the soft circumferential segment.

26. The catheter of claim 13, wherein the circumferential segments extend in the longitudinal direction substantially along the entire length of the distal section.

* * * * *